United States Patent
Kukuk et al.

(10) Patent No.: US 8,265,731 B2
(45) Date of Patent: Sep. 11, 2012

(54) APPARATUS AND METHOD FOR ALIGNING A LIGHT POINTER WITH A MEDICAL INTERVENTIONAL DEVICE TRAJECTORY

(75) Inventors: Markus Kukuk, Palo Alto, CA (US);
Norbert Strobel, Heroldsbach (DE);
Sandy Napel, Menlo Park, CA (US);
Rebecca Fahrig, Palo Alto, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 829 days.

(21) Appl. No.: 11/970,707

(22) Filed: Jan. 8, 2008

(65) Prior Publication Data

US 2008/0194945 A1    Aug. 14, 2008

Related U.S. Application Data

(60) Provisional application No. 60/889,568, filed on Feb. 13, 2007.

(51) Int. Cl.
*A61B 5/05* (2006.01)
(52) U.S. Cl. ......... 600/424; 600/426; 600/407; 362/259
(58) Field of Classification Search .......... 600/424–429; 606/129–130, 198
See application file for complete search history.

(56) References Cited

U.S. PATENT DOCUMENTS

| | | | | |
|---|---|---|---|---|
| 5,389,101 A * | 2/1995 | Heilbrun et al. | | 606/130 |
| 5,732,703 A * | 3/1998 | Kalfas et al. | | 600/407 |
| 5,792,215 A | 8/1998 | Martin et al. | | |
| 6,317,266 B1 * | 11/2001 | Yoshimura et al. | | 359/619 |
| 6,810,280 B2 | 10/2004 | Strobel | | |
| 6,811,313 B2 | 11/2004 | Graumann et al. | | |
| 2006/0235435 A1 * | 10/2006 | Soerensen et al. | | 606/130 |
| 2006/0235849 A1 * | 10/2006 | Schmidt et al. | | 707/7 |
| 2007/0208252 A1 * | 9/2007 | Makower | | 600/424 |
| 2008/0015569 A1 * | 1/2008 | Saadat et al. | | 606/41 |
| 2008/0119722 A1 * | 5/2008 | Swaney | | 600/415 |

* cited by examiner

*Primary Examiner* — Tse Chen
*Assistant Examiner* — Joel F Brutus
(74) *Attorney, Agent, or Firm* — Alexander J Burke

(57) ABSTRACT

A pointing light device includes a light pointer, such as a laser pointer; and an elongated pointing member detachably associated with the light pointer. The pointing member contains at least two bead-like members. Also, a method for aligning a light pointer with a predetermined medical interventional device trajectory. The method includes attaching a pointing member to an output end the light pointer to form a movable pointing light device; imaging two or more bead-like members of the pointing member to create live projection images or shadows in the live projection image; projecting at least first and second points associated with the predetermined medical interventional device trajectory onto the live projection image; and moving the pointing light device until the live projection images of the two members are aligned with corresponding ones of the projected first and second points in the live projection image.

25 Claims, 7 Drawing Sheets

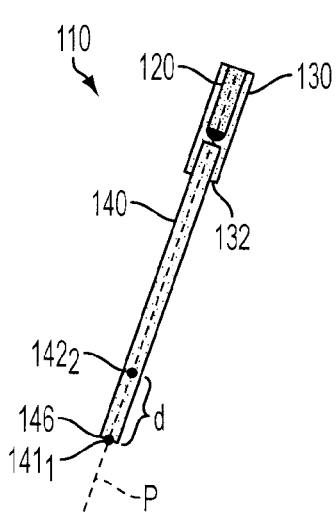 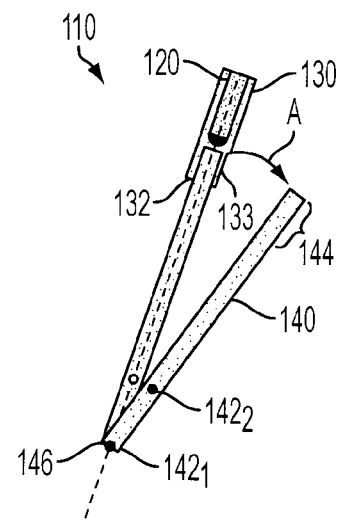
FIG. 1A          FIG. 1B
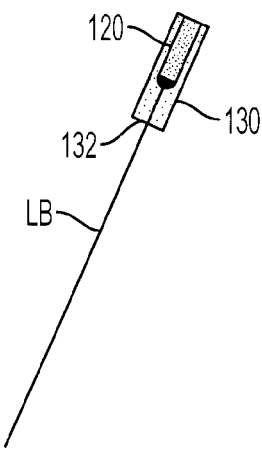
FIG. 1C

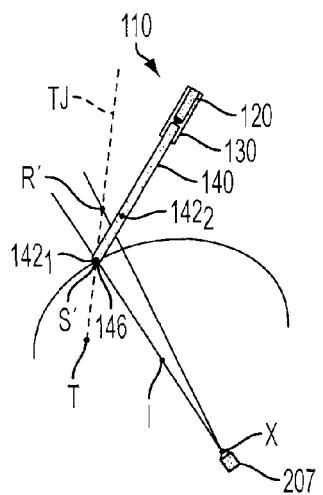
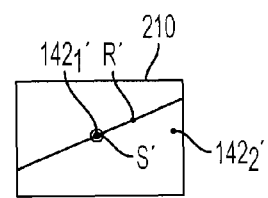
FIG. 9A　　　　　　　　FIG. 9B
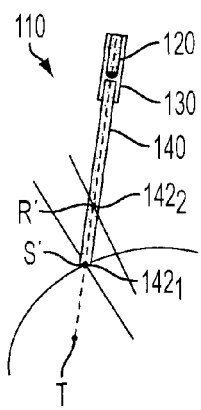
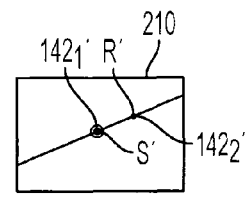
FIG. 10A　　　　　　　FIG. 10B

APPARATUS AND METHOD FOR ALIGNING A LIGHT POINTER WITH A MEDICAL INTERVENTIONAL DEVICE TRAJECTORY

RELATED APPLICATIONS

This application claims the benefit of U.S. Provisional Application Ser. No. 60/889,568 filed on Feb. 13, 2007, the entire disclosure of which is incorporated herein by reference.

FIELD OF THE INVENTION

The invention relates to imaging-guided medical interventional procedures. More particularly, the invention relates to an apparatus and method for aligning a light pointer with a predetermined medical interventional device trajectory.

BACKGROUND OF THE INVENTION

Percutaneous needle procedures, such as needle biopsies, drainages, and other medical interventional procedures, are routinely performed using x-ray fluoroscopy-guided methods. In an attempt to reduce procedure time and radiation exposure, while improving targeting accuracy, the use of laser pointer devices has been proposed. A conventional laser pointer-based workflow may include four phases: image acquisition, medical interventional device (needle) trajectory planning, light pointer aligning, and needle puncture.

In the image acquisition phase, a three-dimensional (3D) image of the patient is either directly acquired using a C-arm CT system or a CT or MRI scanner. In the case of a 3D image obtained using the CT or MRI scanner, the 3D image must then be registered to a C-arm system.

The needle trajectory planning phase involves marking a target point (e.g., a tumor) and a suitable skin entry point on the 3D image The ideal needle trajectory is determined by a straight line that originates outside the patient's body and passes through the skin entry point and the target point.

The light pointer aligning phase involves aligning the light beam of a laser pointer with the needle trajectory determined by the above-described line. The spot of light generated on the skin of the patient's body provides a visible guide for needle placement.

In the needle puncture phase, the tip of the needle is placed on the laser light sot on the patient's skin and oriented such that the laser light spot is visible in the center of the needle hub. The needle is then advanced forward by keeping the laser light spot centered on the needle hub. The needle is commonly imaged in two-dimensions (2D) using x-ray fluoroscopy while it is advanced towards the target.

Several methods have been proposed for aligning the laser with the planned needle trajectory in the light pointer aligning phase. One particular class of methods uses a passive mechanical arm for holding the laser pointer device in place and x-ray fluoroscopy for aligning the laser pointer device.

An example of one method in this class associated with C-arm hybrid (2D/3D) imaging systems is known as the "bulls-eye view" or "down the beam/barrel view" method. This method includes four steps (after image acquisition and needle trajectory planning):
1. Isocentering the needle target on the C-arm system.
2. Rotating the C-arm so that the target point and skin entry point are collinear with the central x-ray beam (bulls-eye, down-the-beam view).
3. Aligning needle with the central x-ray beam.
4. Aligning the laser with the needle.

In step 1, the C-arm system is adjusted such that the target point is as close as possible to the isocenter of the C-arm. This can be done by forward projecting the target point onto the detector of the system and placing a graphical marker (dot) at this position onto the live fluoroscopic image. This functionality is typically available with imaging systems with a known projection geometry (calibrated x-ray cameras). Then, the C-arm table is adjusted (in the x, y, and z directions) so that the dot appears in the center of the fluoroscopic image in two orthogonal views.

After the target point coincides with the isocenter, the C-arm is rotated in step 2 so that the central beam, passing from the x-ray source of the system through the isocenter to the center pixel of the detector, passes through the skin entry point as well. Under such a projection geometry, the target and skin entry points appear superimposed on top of each other and the central beam and the planned needle trajectory are collinear.

In step 3, the needle is aligned with central beam under live fluoroscopy by placing the needle tip over the graphical marker on the skin entry point and adjusting the orientation of the needle so that it projects to a point instead of a line.

Finally in step 4, the laser is aligned with the needle by keeping the needle in place, while adjusting the mechanical arm so that the laser light beam is collinear with the needle.

An improvement to this method has been proposed that eliminates one of the above mentioned four steps:
1. Isocentering.
2. Assuming bulls eye view.
3. Aligning laser with central beam.

After isocentering and assuming the bulls-eye view, the laser is directly aligned with the central beam, without the need for placing the needle first under live fluoroscopy. This is done by simply placing the laser into the center of the detector, orthogonal to the detector plate by using a mechanical guide, which first needs to be attached to the detector and later removed.

There are shortcomings with both these methods. The first method is time consuming, placing the target point into the isocenter of the C-arm is difficult to achieve with adequate accuracy, and aligning the laser by first aligning the needle is cumbersome and time consuming and typically requires two persons to perform. The second method requires isocentering and the use of mechanical guides to align the laser.

Accordingly, a method and apparatus for aligning a laser pointing device with a pre-planned medical interventional device trajectory is needed that avoids the shortcomings of current methods and apparatus.

SUMMARY

Disclosed herein is a pointing light device comprising: a light pointer; and a pointing member detachably associated with the light pointer. The pointing member contains at least two members, which when imaged, are capable of being viewed in a live projection image.

Also disclosed herein is a method for aligning a light pointer with a predetermined medical interventional device trajectory. The method comprises the steps of: attaching a pointing member to an output end of the light pointer to form a movable pointing light device, the pointing member including at least two members, which when imaged, are capable of being viewed in a live projection image; imaging the at least two members of the pointing member to create live projection images of the at least two members in the live projection image; projecting at least first and second points onto the live projection image, the first point being at or above a location where a medical interventional device will enter the patient, the first and second points lying on the predetermined medical interventional device trajectory; and moving the pointing light device until the live projection images of the at least two members of the pointing member are aligned with corresponding ones of the projected first and second points in the live projection image.

BRIEF DESCRIPTION OF THE DRAWINGS

FIGS. 1A-1C are schematic diagrams of an exemplary embodiment of a pointing light device for use in defining a skin entry point and direction of access in imaging-guided medical interventional procedure.

FIGS. 9A and 10A are schematic diagrams showing the pointing light device being aligned with alignment markers.

FIGS. 9B and 10B are schematic diagrams of the live 2d x-ray image as the pointing light device is being aligned with the alignment markers in respective FIGS. 9A and 10A.

DETAILED DESCRIPTION OF THE INVENTION

Figure 2:
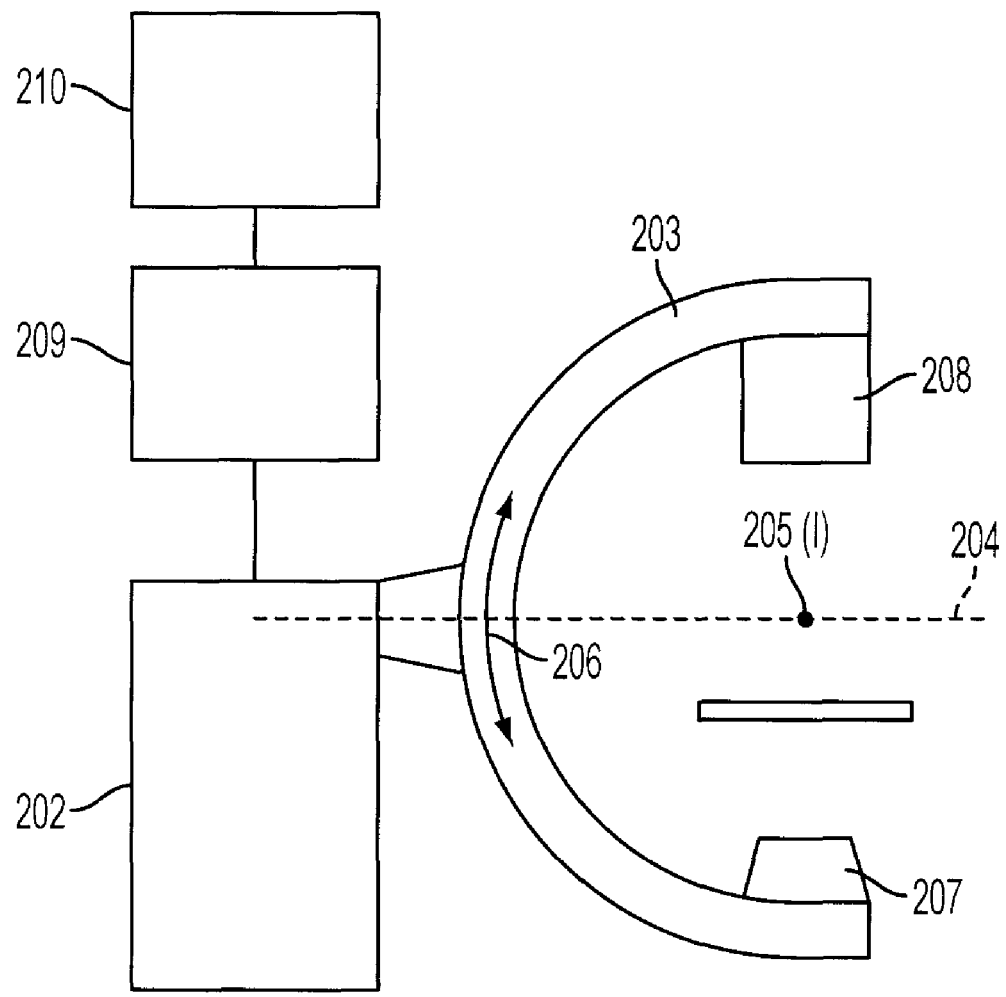
FIG. 2 is a schematic diagram of an exemplary embodiment of the C-arm CT x-ray fluoroscopy system.

FIGS. 1A-1C collectively show an exemplary embodiment of a pointing light device for use in defining a skin entry point and direction of access in imaging-guided medical interventional procedure, denoted by reference character 110. The device 110 includes a light pointer 120 contained in a housing 130 and an elongated radio-lucent pointing member 140 (stick pointer) detachably connected within an output end 132 of the housing 130 so that the stick pointer 140 is inline or co-linear with the light pointer 120. The light pointer 120 may comprise any device that is capable of generating a collimated beam of light. In a preferred embodiment, the light pointer 120 comprises a laser pointer.

The stick pointer 140 includes two or more 3D members, which when imaged, are capable of being viewed in a live projection image. The two or more members are disposed at known positions in or on the stick pointer 140. In operation, the 3D members are projected as 2D shadows onto a real-time (live) 2D x-ray image, as will be explained further on. In the shown embodiment, the two or more 3D members comprise two radio-opaque beads $142_1$, $142_2$. The beads $142_1$, $142_2$ may be of any suitable shape including, without limitation, spherical, oval, square, rectangular, triangular, irregular, and star-shape. The beads $142_1$, $142_2$ may have the same or different shapes. The beads $142_1$, $142_2$ may be made of any suitable material capable of being viewed in a live projection image including, without limitation, lead and steel, to name a few.

Bead $142_1$ may be partially embedded within the stick pointer 140 so that an exposed portion of the bead $142_1$ forms a free end 146 (first position) of the stick pointer 140. Alternately, bead $142_1$ may be fully embedded within the stick pointer 140 so that no portion of the bead $142_1$ is exposed at the free end 146 (first position) of the stick pointer 140. Still further, bead $142_1$ may be fully embedded within the stick pointer 140 and spaced a known distance from the free end 146 (first position) of the stick pointer 140. Bead $142_2$ may be fully embedded within the stick pointer 140 at a fixed or an adjustable second position within the stick pointer 140. In one exemplary embodiment, the beads $142_1$, $142_2$ do not contact one another and are separated by a known distance d measured, for example, between the centers or outer surfaces of the beads $142_1$, $142_2$. Alternatively, the bead $142_2$ may be embedded within the stick pointer 140 at a fixed location such that bead $142_2$ contacts bead $142_1$.

In embodiments where more than two 3D members or beads $142_1$, $142_2$ are used in the stick pointer 140, the spacing between the members or beads $142_1$, $142_2$ can be arbitrary, i.e., differ from bead to bead, as long as the spacings between all members including beads $142_1$, $142_2$ are known or can be determined. Stick pointers having more than two radio-opaque members or beads may improve accuracy, but also increase the number of points or markers that must be observed. Only two of the members or beads $142_1$, $142_2$, in such embodiments, need be visible in the live 2D x-ray image for proper operation of the stick pointer 140. Hence, the distance d between the radio-opaque members or beads should be selected to ensure that at least two members or beads project onto a detector of an imaging apparatus that will be used for imaging the interventional device. If the beads are placed too far apart, some of them may not project onto the detector.

Referring still to FIGS. 1A-1C, the light pointer 120 is constructed and adapted to generate a collimated light beam LB having a path P that passes through the centers of the members or beads $142_1$, $142_2$.

The pointing light device 110 may be mounted on a multiaxial mounting arm structure (not shown) that allows the device to be pivoted about an x-axis, a y-axis, and a z-axis. The arm structure may be motor operated and controlled remotely from a controller. Such mounting structures and controllers are well known in the art and therefore, are not described further herein.

As shown in FIG. 1B, the output end 132 of the housing 130 further includes a release mechanism that allows the stick pointer 140 to be detached from within the output end 132 of the housing. In one embodiment, the release mechanism may comprise a longitudinal opening or slot 134 formed in the output end 132 of the housing 130 that is sized to allow a proximal end portion 144 of the stick pointer 140 which is disposed within the output end 132 of the housing 130 when the stick pointer 140 is attached thereto to move through the slot 134 so that the stick pointer 140 can be detached sideways from the housing 130, as shown by arrow A. A detent (not shown) may be provided within the slot 134 to prevent the stick pointer 140 from moving freely through the slot 134. The housing 130 may also include a switch arrangement (not shown) that coacts with the proximal end portion 144 of the stick pointer 140 and light pointer 120 to automatically turn on the light beam LB of the light pointer 120 when the proximal end portion 144 of the stick pointer 140 is removed from within the output end 132 of the housing 130. In an alternate embodiment, the proximal end portion 144 of the stick pointer 140 may be constructed to telescopically collapse into or around the stick pointer 140 to form the release mechanism, so that the stick pointer 140 can be axially detached from the housing 130.

The imaging-guided medical interventional procedure may be performed using a real-time imaging system. In one exemplary embodiment, the real-time imaging system is a hybrid C-arm-based X-ray fluoroscopy system also providing 3D imaging capabilities (C-arm CT). Such a system may be referred to as a C-arm CT X-ray fluoroscopy system. Other embodiments of the method may use other suitable real-time imaging systems.

FIG. 2 shows an exemplary embodiment of the C-arm CT x-ray fluoroscopy system. The C-arm CT x-ray fluoroscopy system includes a base frame 202 and a C-arm 203 mounted to the base frame 202 so that it is capable of being rotated around axis 204 (angulation) and turned around axis 205 in the direction of the double arrow 206 (orbital rotation). An x-ray source 207 and an x-ray detector 208 are mounted 180 degrees opposite one another adjacent the ends of the C-arm 203. The C-arm isocenter, I, coincides with the intersection of axis 204 and axis 205. An image recording and calculating device 209 is provided to control image recording and output operations, movement of the C-arm 203 and to control the x-ray source 207 and the x-ray detector 208. A monitor 210 is provided for viewing images outputted from the image recording and calculating device 209.

The pointing light device 110 is preferably used for, but is not limited to, defining a skin entry point and direction of access in an imaging-guided medical interventional procedure. In such procedure, the pointing light device 110 is aligned along a trajectory that has been planned in advance (pre-planned) for a medical interventional device (e.g. needle). This may be accomplished by placing a distal tip (free end 146 formed by bead $142_1$) of the pointing light device 110 onto an entry point on the patient's skin and maneuvering a proximal end of the pointing light device 110 in a pivotal manner using the skin entry point as a pivot point until image projections of the radio-opaque members or beads $142_1$, $142_2$ match-up or align with corresponding, pre-determined target markers in a live 2D image produced by the imaging system.

Figure 3:
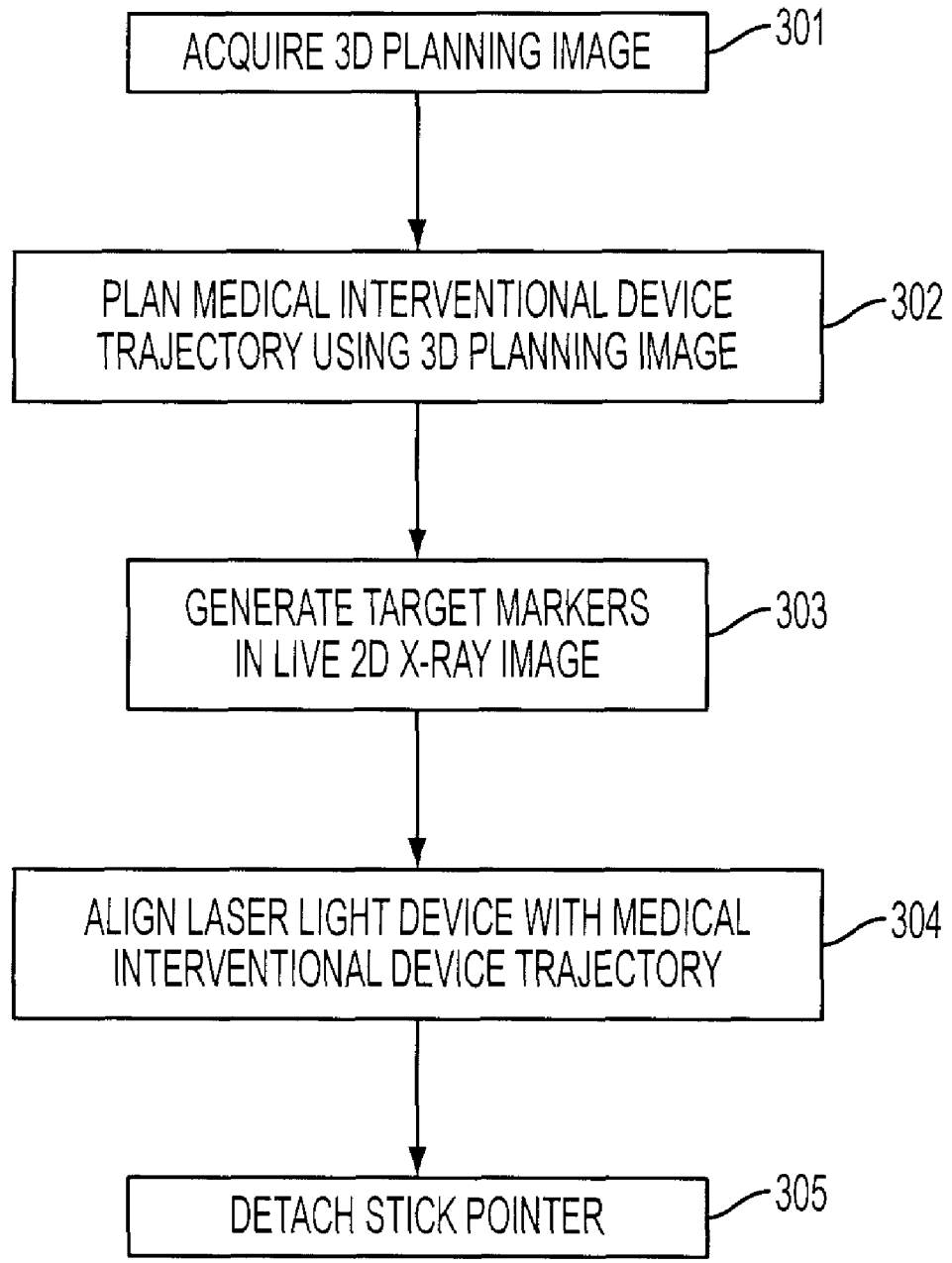
FIG. 3 is a flowchart of an exemplary embodiment of a method for defining a skin entry point and direction of access in an imaging-guided medical interventional procedure, using the pointing light device.

FIG. 3 is a flowchart of an exemplary embodiment of a method for defining a skin entry point and direction of access in an imaging-guided medical interventional procedure, using the laser light device. The method will be described in the context of the earlier described C-arm X-ray fluoroscopy system. Persons of ordinary skill in the art will appreciate that the method may be performed using other suitable types of real-time imaging systems.

Figure 4:
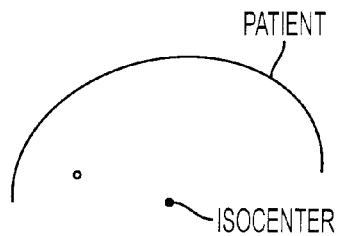
FIG. 4 is a schematic diagram of a 3D planning image.

In step 301 of the method, a 3D interventional procedure planning image of a patient is acquired. The 3D planning image comprises a plurality of 2D projection images reconstructed to form a 3D image. Such 3D images are well known in the medical imaging art and are commonly referred to in the art as C-arm CT images. The 3D planning image, shown in FIG. 4, may be acquired using the C-arm CT x-ray fluoroscopy system. In other embodiments, a CT or MRI scanner may be used for acquiring the 3D data sets needed to carry out planning. In such embodiments, an additional registration step or process may be required to register the 3D planning image to the imaging system, e.g., a C-arm X-ray fluoroscopy system. Since such registration methods are well known in the art, no further description of same is needed herein.

Figure 5:
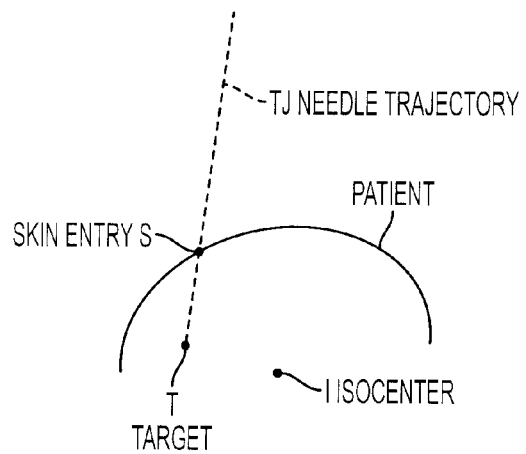
FIG. 5 shows target and skin entry points that have been identified in the 3D planning image of figure and a medical interventional device trajectory defined by the target and skin entry points.

In step 302, the 3D planning image acquired in step 301 is used for planning the medical interventional device trajectory. The interventional medical device trajectory is planned by marking a target point, T, (e.g., a tumor) and a suitable skin entry point, S, in the 3D image, as shown in FIG. 5. As will be explained further on, the user selected 3D skin entry point, S, will be projected as a 2D target or alignment marker, S', onto a live 2D image of the patient generated by the C-arm CT x-ray fluoroscopy system. The medical interventional device trajectory is determined by a straight line, TJ, that originates outside the patient and passes through the 3D user selected skin entry point, S, and the target point, T.

In step 303, 2D target or alignment markers S' and R' are projected onto a live 2D x-ray image of the patient that is displayed on the monitor 210 (FIG. 8B) of the C-arm CT X-ray fluoroscopy system (x-ray imaging system), using the medical interventional device trajectory, TJ, obtained in the 3D planning image of step 302. Further on in the method, the 3D radiopaque beads $142_1$, $142_2$ of the stick pointer 140 will be projected as respective 2D shadows $142_1'$, $142_2'$ (FIGS. 9B and 10B) onto the live 2D x-ray image of the patient by the x-ray imaging system and aligned with corresponding 2D alignment markers S' and R' in the live 2D x-ray image of the patient by maneuvering the pointing light device 110. In one exemplary embodiment, the alignment markers may be represented by graphical symbols, geometric shapes, colored dots, etc., that are overlaid onto the live 2D x-ray image displayed on the monitor 210 of the x-ray imaging system.

The positions of the alignment markers S' and R' are determined in step 303 by assuming that the distal end 146 of the stick pointer 140 touches the patient's skin at skin entry point S or is disposed immediately above the skin entry point S (on the medical interventional device trajectory) and that the stick pointer 140 containing the radio-opaque beads $142_1$, $142_2$ is aligned with the medical interventional device trajectory TJ planned in step 302. It is also assumed that the C-arm imaging system is calibrated, which means that the C-arm system's projection geometry is known. Therefore it is possible to mathematically forward project any 3D alignment marker onto the detector (image plane) to yield its corresponding 2D alignment point. In other words, it is possible to calculate where the 3D radio-opaque beads $142_1$, $142_2$, when placed in the field of view of the x-ray imaging system, will show up in the live x-ray image.

Figure 6A:
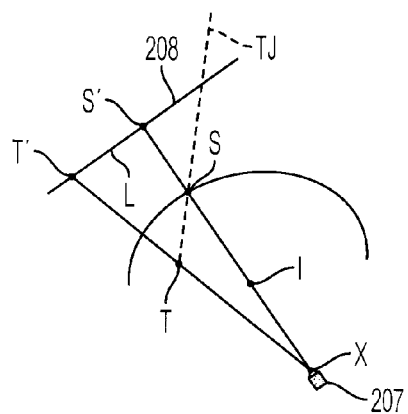
FIG. 6A is a schematic diagram showing projection geometries of the target and skin entry points.

The following discussion sets forth one exemplary process for performing step 303. In this process, the target and skin entry points T and S of the 3D planning image (FIG. 5) obtained in step 302 are projected onto the live 2D x-ray image shown on the monitor 210 of the C-arm x-ray imaging system, as shown in FIG. 6A. This is accomplished by generating an X-ray beam with the X-ray source 207 which passes through the C-arm's isocenter, I, and is close to the target point, T, thereby forward projecting the 3D target point, T, and the 3D skin entry point, S, onto the X-ray detector 208 of the X-ray imaging system the target point, T (the skin entry point, S, target point T, and x-ray source point, X, define a plane in 3D space which intersects the X-ray image detector in a line L), as 2D point T' and 2D alignment marker S'. This process is possible on C-arms with a calibrated x-ray imaging system (known projection geometry).

Figure 6B:
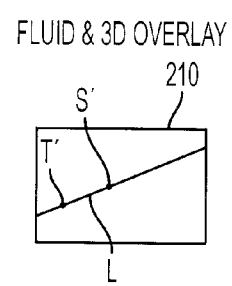
FIG. 6B is a schematic diagram showing the 3D planning image blended into a live 2D x-ray image shown on a monitor of a C-arm CT x-ray imaging system.

The field of view in the live 2D X-ray image is then evaluated to determine if the 3D skin entry point, S, is being projected as 2D alignment marker, S', into an approximately central location of the live 2D image of the patient. If the alignment marker, S', is not in this location, the C-arm 203 of the C-arm X-ray imaging system is rotated so that the target marker, S', is projected onto approximately the center of the live 2D X-ray image shown on the monitor 210 of the C-arm X-ray imaging system (FIG. 6B), or any other desired position. Approximately centering the alignment marker, S', in the live 2D X-ray image ensures that the shadows of the medical interventional device (not shown) and the shadows of radio-opaque beads $142_1'$, $142_2'$ of the stick pointer 140 remain in the field of view of the x-ray system during the laser light device alignment phase.

Figure 7:
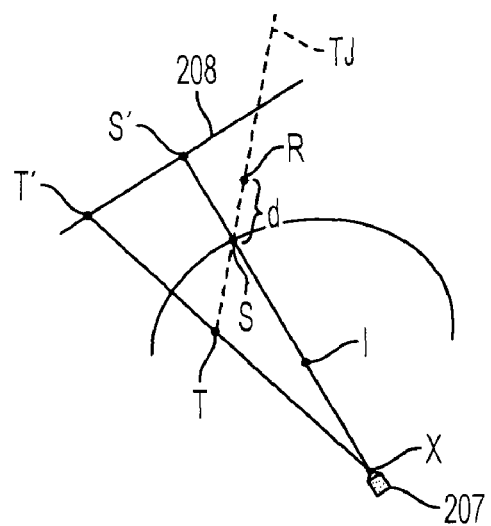
FIG. 7 is a schematic diagram showing a projection geometry of an additional point located from the skin entry point on the medical interventional device trajectory TJ.

Further in step 303, a 3D point R on the medical interventional device trajectory TJ is calculated, which is located from the skin entry point S by a distance d, as shown in FIG. 7. Point R is projected into the live 2D x-ray image as a 2D point R'. Skin entry point S represents the distal-most radio-opaque bead $142_1$ of the stick pointer 140 and point R represents the other radio-opaque bead $142_2$ of the stick pointer (assuming a two-bead stick pointer). The distance d corresponds to the known distance between the two radio-opaque beads $142_1$, $142_2$ (typically but not limited to the center-to-center distance between the beads). In embodiments where the stick pointer has more than two radio-opaque beads, additional points corresponding to the additional beads would be mathematically calculated along the medical interventional device trajectory TJ using the known distances between the beads.

Figure 8A:
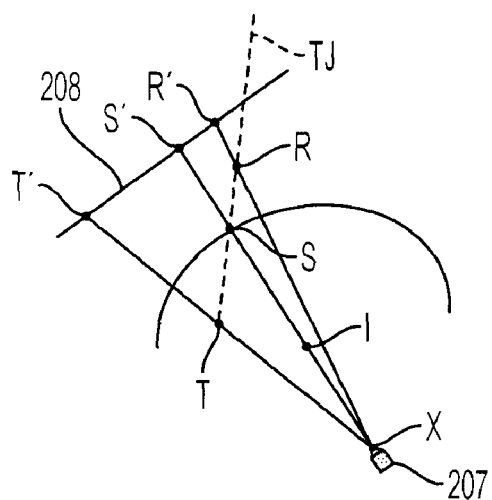
FIG. 8A is a schematic diagram showing the projection of the target point, the skin entry point, and the additional point, onto the x-ray detector.
Figure 8B:
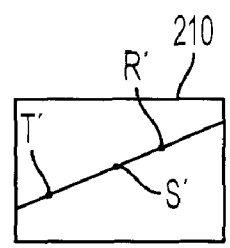
FIG. 8B is a schematic diagram of the live 2D x-ray image resulting from the projection of the target point, the skin entry point, and the additional point onto the x-ray detector.
Figure 11:
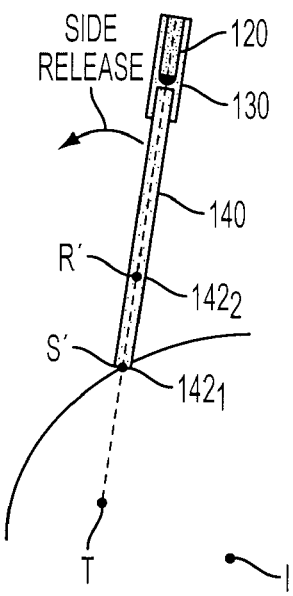
FIG. 11 is a schematic diagram showing the detachment of the stick pointer from the housing of the pointing light device.

As shown in FIG. 8A, points T, S, and R are projected onto the x-ray detector as point T', S' and R'. Point T' is collinear to the line between X and T, point S' collinear to the line between and X and S, and point R' is collinear to the line between X and R. The projected collinear points S' and R' are the desired alignment markers projected onto the live 2D x-ray image displayed on the monitor 210 of the C-arm x-ray imaging system, as shown in FIG. 8B.

In step 304, the pointing light device 110 is aligned with the medical interventional device trajectory TJ under the live 2D X-ray imaging. This process involves manipulating the mounting arm structure holding the pointing light device 110 so that a distal end 146 of the stick pointer 140 is positioned to touch the patient's skin at the skin entry point S, as shown in FIG. 9A (or is disposed immediately above the skin entry point S at a known distance from the point S, e.g., in embodiments where the stick pointer 140 may be resting on a gauze pad, etc., disposed between the skin and the distal end 146 of the pointer). This causes an X-ray shadow $142_1'$ of the radio-opaque bead $142_1$ in the distal end of the stick pointer 140 to be superimposed or projected on its associated alignment marker S', as shown in FIG. 9B.

In FIG. 10A, the mounting arm structure is then further manipulated to pivot the end of the pointing light device 110 containing the light pointer 120, using the distal end-to-skin contact point as a pivot point, until an X-ray shadow $142_2'$ of the other bead $142_2$ is superimposed or projected onto its corresponding alignment marker R', as shown in FIG. 10B. This process aligns the light beam path P of the light pointer 120 with the planned medical interventional device trajectory TJ.

Persons of ordinary skill in the art will appreciate that bead shadow-to-alignment marker correspondence ambiguities can be resolved in the method by projecting alignment markers S' and R' that can be visually distinguished from the X-ray shadows of the beads $142_1'$, $142_2'$, e.g. by generating the alignment markers S' and R' in a size(s) which is(are) larger than the size(s) of the shadows of the beads $142_1'$, $142_2'$ as shown in FIGS. 9B and 10B, in a different shape(s) than the shape(s) of the shadows of the beads $142_1'$, $142_2'$ or in a color(s) different from the color shadows of the beads $142_1'$, $142_2'$ (which are typically gray in the live projection image). Ambiguities between the alignment markers S' and R' may also exist and can be resolved in the method by generating them in different colors, shapes, and sizes so that they can be easily distinguished from one another as well as from the x-ray shadows of the beads $142_1'$, $142_2'$.

Once alignment has been achieved, in step 305, the stick pointer 140 is detached from the output end of the housing 130 containing the light pointer 120. As described earlier, the release mechanism of the stick pointer 140 allows it to be detached sideways in the direction of arrow A from the output end 132 of the housing 130 containing the light pointer 120 (or detached axially in the case of a telescopically collapsible stick pointer 140). Removal of the stick pointer 140 automatically switches on the laser light of the laser pointer 120.

Figure 12:
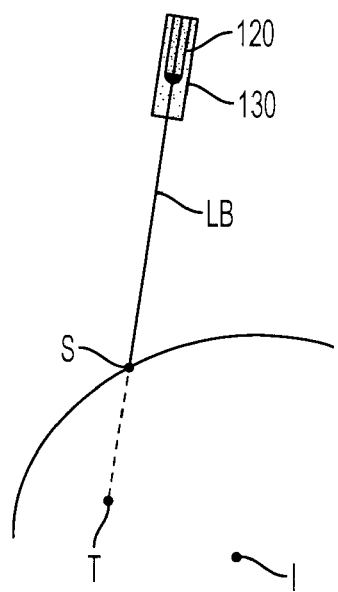
FIG. 12 is a schematic diagram showing automatic activation of the light pointer of the pointing light device during the detachment of the stick pointer from the housing.

As shown in FIG. 12 the light beam LB of the light pointer 120 visually displays the medical interventional device trajectory TJ. The medical interventional device (not shown) can now be placed and advanced in known manner.

The method and apparatus may be embodied in other specific forms without departing from the spirit or essential attributes of the disclosure. Accordingly, reference should be made to the appended claims, rather than the foregoing specification, as indicating the scope of the invention.

What is claimed is:

1. A method for aligning a light pointer with a predetermined medical interventional device trajectory, the method comprising the steps of:
    attaching a pointing member to an output end of the light pointer to form a movable pointing light device, the pointing member including two or more radio-opaque members, which when imaged, are capable of being recognized in a live projection image;
    radiation imaging said two or more radio-opaque members of the pointing member to create a live projection image of said two or more radio-opaque members and patient internal anatomy in the live projection image;
    projecting at least first and second points onto the live projection image, the first point being at or above a location where a medical interventional device enters the patient, the first and second points lying on the predetermined medical interventional device trajectory; and
    enabling moving the pointing light device until the live projection image indicates said two or more radio-opaque members of the pointing member are aligned with corresponding ones of the projected first and second points in the live projection image.

2. The method according to claim 1, wherein
    said two or more radio-opaque members are a known distance apart and said distance is used in said projecting said at least first and second points onto the live projection image,
    said radiation imaging comprises at least one of, (a) X-ray and (b) CT scan, imaging and the projecting step is performed with an imaging system having a C-arm, the projecting step including positioning the C-arm such that the first point appears approximately in a center of the live projection image.

3. The method according to claim 1, wherein a first one of said two or more radio-opaque members at least partially defines a free end of the pointing member and the moving step includes contacting the free end of the pointing member to the location on the patient where the medical interventional device will enter to align the live projection image of the first one of said two or more radio-opaque members with the projected first point in the live projection image.

4. The method according to claim 2, wherein a second one of said two or more radio-opaque members of the pointing member is disposed at a known distance from the first one of the at least two members and the moving step further includes pivoting the pointing light device until the live projection image of the second one of said two or more radio-opaque members aligns with the projected second point in the live projection image.

5. The method according to claim 1, wherein the second point is calculated using the medical interventional device trajectory and a distance between said two or more radio-opaque members.

6. The method according to claim 1, wherein said radiation imaging comprises at least one of, (a) X-ray and (b) CT scan, imaging.

7. The method according to claim 1, wherein the two or more radio-opaque members comprise radiolucent members.

8. The method according to claim 1, wherein the imaging step is performed with a C-arm X-ray system and the live image is comprises an X-ray image.

9. The method according to claim 1, further comprising the step of detaching the pointing member from the pointing light device.

10. The method according to claim 9, wherein the detaching step is performing by detaching the pointing member sideways from the pointing light device.

11. The method according to claim 1, further comprising the step of turning on the light pointer.

12. The method according to claim 11, wherein the light pointer turning on step includes the step of detaching the pointing member from the pointing light device.

13. The method according to claim 12, wherein the light pointer is a laser light device and
the detaching step is performing by detaching the pointing member sideways from the laser light device.

14. The method according to claim 9, wherein the detaching step is performing by axially detaching the pointing member from the pointing light device.

15. The method according to claim 12, wherein the detaching step is performed by axially detaching the pointing member from the pointing light device.

16. A pointing light device comprising:
a light pointer; and
a pointing member detachably associated with the light pointer, the pointing member containing two or more radio-opaque members, which when imaged by a radiation imaging system, are capable of being identified in a live projection image through patient internal anatomy and are movable until the live projection image indicates said two or more radio-opaque members of the pointing member are aligned with corresponding ones of projected first and second points in the live projection image.

17. The pointing light device according to claim 16, further comprising a housing for containing the light pointer and said radiation imaging system comprises at least one of, (a) an X-ray and (b) a CT scan, imaging system, said pointing light device being aligned with a predetermined medical interventional device trajectory by moving the pointing light device until the live projection images of said two or more radio-opaque members of the pointing member are aligned with corresponding projected first and second points in the live projection image.

18. The pointing light device according to claim 17, wherein the pointing member is detachably connected to the housing, said pointing light device being aligned with a predetermined medical interventional device trajectory by projecting at least first and second points onto the live projection image, the first point being at or above a location where a medical interventional device enters the patient, the first and second points lying on the predetermined medical interventional device trajectory.

19. The pointing light device according to claim 18, further comprising a release for allowing the pointing member to be detached sideways from the housing.

20. The pointing light device according to claim 18, further comprising a release for allowing the pointing member to be axially detached from the housing.

21. The pointing light device according to claim 16, further comprising a switch for turning on the light pointer when the pointing member is detached from the housing.

22. The pointing light device according to claim 16, wherein said pointing light device is aligned with a predetermined medical interventional device trajectory by moving the pointing light device until the live projection images of said two or more radio-opaque members of the pointing member are aligned with corresponding projected first and second points in the live projection image.

23. The pointing light device according to claim 16, wherein the two radio-opaque members comprise radiolucent members.

24. The pointing light device according to claim 16, wherein a first one of said two or more radio-opaque members at least partially defines a free end of the pointing member.

25. The laser light device according to claim 24, wherein a second one of said two or more radio-opaque members of the pointing member is disposed at a known distance from the first one of said two or more radio-opaque members.

* * * * *